US012653745B2

(12) United States Patent
Miller et al.

(10) Patent No.: US 12,653,745 B2
(45) Date of Patent: Jun. 16, 2026

(54) METHOD AND APPARATUS FOR SECURING A PATIENT'S LIMB

(71) Applicant: Kyra Medical, Inc., Northborough, MA (US)

(72) Inventors: Howard P. Miller, Concord, MA (US); Thomas K. Skripps, Acton, MA (US); Justin McCarthy, Boxborough, MA (US)

(73) Assignee: KYRA MEDICAL, INC.

( * ) Notice: Subject to any disclaimer, the term of this patent is extended or adjusted under 35 U.S.C. 154(b) by 15 days.

(21) Appl. No.: 18/828,462

(22) Filed: Sep. 9, 2024

(65) Prior Publication Data

US 2024/0423859 A1 Dec. 26, 2024

Related U.S. Application Data

(63) Continuation of application No. 18/117,538, filed on Mar. 6, 2023, now Pat. No. 12,083,053, which is a
(Continued)

(51) Int. Cl.
| | |
|---|---|
| *A61F 5/05* | (2006.01) |
| *A61F 5/01* | (2006.01) |
| *A61G 13/12* | (2006.01) |

(52) U.S. Cl.
CPC ........ *A61G 13/1245* (2013.01); *A61F 5/0111* (2013.01); *A61G 13/125* (2013.01);
(Continued)

(58) Field of Classification Search
CPC ................ A61G 13/125; A61G 13/126; A61G 13/1245; A61G 13/128; A61G 2203/78;
(Continued)

(56) References Cited

U.S. PATENT DOCUMENTS

| | | | |
|---|---|---|---|
| 1,666,783 A | 4/1928 | Kries | |
| 2,052,990 A * | 9/1936 | Siebrandt .............. | A61F 5/0585 |
| | | | 602/35 |

(Continued)

FOREIGN PATENT DOCUMENTS

| | | |
|---|---|---|
| EP | 1014911 A1 | 7/2000 |
| EP | 2679203 A1 | 1/2014 |
| WO | 9844890 A1 | 10/1998 |

OTHER PUBLICATIONS

The foreign references and the NPLs are not submitted herewith as they can be retrieved in the Parent U.S. Appl. No. 18/117,538, filed Mar. 6, 2023.

*Primary Examiner* — Camtu T Nguyen
(74) *Attorney, Agent, or Firm* — Potomac Law Group, PLLC; John J. Penny, Jr.

(57) ABSTRACT

A limb support apparatus and corresponding methods for making same are disclosed. The limb support can comprise a shell for supporting a patient's limb during treatment, examination, and/or recovery. The shell can comprise at least one padding configured to protect the patient's limb. The padding can be secured to the shell using one or more mounting structures included in the padding. The mounting structures are configured such that they are received by corresponding mounting openings and/or features in the shell. An interference fit between the mounting structures and mounting openings/features secures the padding against the shell, thereby preventing the padding from inadvertently moving or sliding on the shell. Embodiments disclosed herein eliminate the need for traditionally used fasteners that are often difficult to clean and sterilize, thereby improving the quality of patient care and facilitating cleaning of patient and/or operating rooms.

6 Claims, 16 Drawing Sheets

Related U.S. Application Data continuation of application No. 16/249,813, filed on Jan. 16, 2019, now Pat. No. 11,596,569.

(60) Provisional application No. 62/709,380, filed on Jan. 16, 2018.

(52) U.S. Cl.
 CPC .... *A61G 13/126* (2013.01); *A61F 2005/0172* (2013.01); *A61G 2203/78* (2013.01)

(58) Field of Classification Search
 CPC .... F16B 5/0664; F16B 13/02; A61F 5/05858; A61F 5/05866; A61F 5/05875; A61F 2005/0172; A61F 5/058; A61F 5/0585; A61F 5/05841; A61F 5/0111; A61F 5/0104; A61F 5/0127; A61F 5/0109; A61F 5/0118; A61F 5/0195; A61F 5/013; A43B 5/0429; A43B 5/0405; A41B 3/242
 See application file for complete search history.

(56) References Cited

U.S. PATENT DOCUMENTS

| | | | |
|---|---|---|---|
| 2,057,992 A | 10/1936 | Wiruth | |
| 2,966,905 A | 1/1961 | Kamenshine | |
| 3,049,781 A | 8/1962 | Cochran | |
| 3,640,003 A | 2/1972 | Anderson | |
| 3,762,405 A * | 10/1973 | De George | A61F 5/04 |
| | | | 602/23 |
| 3,834,044 A | 9/1974 | Mc et al. | |
| 4,063,704 A | 12/1977 | Rother | |
| 4,681,097 A * | 7/1987 | Pansiera | A61F 5/0125 |
| | | | 602/16 |
| 4,886,258 A | 12/1989 | Scott | |
| 5,399,152 A * | 3/1995 | Habermeyer | A61F 13/048 |
| | | | 602/23 |
| 5,446,926 A | 9/1995 | Bourque et al. | |
| 5,802,641 A | 9/1998 | Steenburg | |
| 5,961,085 A | 10/1999 | Navarro et al. | |
| 6,058,534 A | 5/2000 | Navarro et al. | |
| 6,263,531 B1 | 7/2001 | Navarro et al. | |
| 6,564,406 B2 | 5/2003 | VanSteenburg et al. | |
| 6,704,959 B2 | 3/2004 | Schuerch | |
| RE41,412 E | 7/2010 | Steenburg | |
| 8,448,274 B2 | 5/2013 | Broens | |
| 10,076,214 B2 | 9/2018 | Aow | |
| 10,188,573 B2 | 1/2019 | Moriarty et al. | |
| 11,020,303 B2 * | 6/2021 | Miller | A61F 5/0111 |
| 11,596,569 B2 * | 3/2023 | Miller | A61G 13/125 |
| 12,083,053 B2 * | 9/2024 | Miller | A61G 13/125 |
| 12,295,894 B2 * | 5/2025 | Diodato | A61G 13/1245 |
| 2006/0225743 A1 | 10/2006 | Schuerch | |
| 2011/0092930 A1 | 4/2011 | Poorman | |
| 2012/0318278 A1 | 12/2012 | Aboujaoude et al. | |
| 2016/0120726 A1 | 5/2016 | Moriarty et al. | |
| 2017/0165143 A1 | 6/2017 | Schuerch, Jr. | |
| 2018/0325715 A1 | 11/2018 | Chung | |
| 2019/0216665 A1 | 7/2019 | Miller et al. | |
| 2019/0254905 A1 | 8/2019 | Lane et al. | |

* cited by examiner

*410*

*777*

1018

1020

810

812

814

816

714

711

818

714

711

820

711

714

824

711

714"

714'

714

822

METHOD AND APPARATUS FOR SECURING A PATIENT'S LIMB

RELATED APPLICATIONS

The present application is a continuation application of, and claims priority under 35 U.S.C. § 120 to, U.S. application Ser. No. 18/117,538, filed on Mar. 6, 2023, which claims priority to U.S. patent application Ser. No. 16/249,813, filed on Jan. 16, 2019, entitled "Method and Apparatus for Securing a Patient's Limb", which claims priority to under 35 U.S.C § 119 and benefit of U.S. Provisional Application No. 62/709,380, filed on Jan. 16, 2018, the entire teachings of which is incorporated by reference herein.

FIELD

The present disclosure generally relates to limb holders, such as limb holders used before, during, and after surgical procedures for supporting patient's limbs, and related methods for making same.

BACKGROUND

During most surgical operations, nurses and surgical and support staff are often responsible for tending to the general health and safety of a patient. For example, nurses and surgical staff often tend to patients while they are under anesthesia and/or while they are recovering after a surgical procedure. In doing so, nurses and surgical staff often consider a variety of factors to ensure a patient's safety. For example, in addition to considering factors for mitigating possible risks associated with the surgical procedure at hand, nurses and hospital staff must also ensure that the patient's possibly unconscious body is also protected from possible physical injuries that may be caused by unwanted movement of the patient's body (e.g., unconscious movements and repositioning of the patient while under anesthesia or sleeping).

To date, various approaches have been developed to standardize the measures used to protect patients, including usage of padding on the surfaces that come in contact with the patient. Since a patient's natural defenses can be inhibited due to anesthesia, normal responses to discomfort or pressure points, which would normally occur if the patient were merely asleep, cannot be relied upon to prevent injury. As such, padding of the surfaces with which the patient's body may come in contact is often used to reduce and mitigate injury to the patient.

For example, the operating table surface in some operating rooms can include a thick pad cover that has been secured to the operating table in order to protect the patient from surface pressure. Supportive devices such as lithotomy stirrups (e.g., used to hold the legs up and apart during surgeries in which the patient is on his/her back or a supine position) can also be padded to mitigate unwanted pressure. Such lithotomy stirrup pads are often held in place using "hook and loop" fastening systems, such as VELCRO® brand fasteners.

Operating rooms can also contain surface and/or airborne contaminates (e.g., bacteria or viruses), which can put patients at the risk of contracting an infection. In fact, infections due to surface or airborne contaminants, such as bacteria or viruses, are among other risks that patients in hospitals and operating rooms can face. For this reason, operating rooms are often cleaned between each procedure, including the padding and other patient contact surfaces.

Generally, any impediment to proper cleaning can put the patients' health and desired recovery at risk.

Although operating rooms, paddings, and other patient surfaces are usually cleaned and disinfected between surgical procedures, any impediment to proper cleaning can put the patients' health and desired recovery at risk. For example, many fastening systems (e.g., traditional hook and loop style fastening systems) used in common lithotomy stirrups are often very difficult to clean. Specifically, traditional hook and loop fasteners can have many cervices, which can in turn render surface cleaning impossible. The loop portion of these fasteners can also be very difficult to surface clean due to its tendency for retaining fluids.

SUMMARY

The present disclosure relates to methods, apparatus, and corresponding systems for securing a patient's limb, for example during a surgical procedure. Embodiments disclosed herein reduce the number of attachments used in traditional limb holders and eliminate parts that are traditionally difficult to sterilize and/or clean.

In one aspects, apparatus and corresponding methods for attaching one or more paddings to a limb support shell is disclosed. The apparatus and corresponding method utilize discrete mating features between the padding(s) and the shell to create a padded support system. The disclosed embodiments can remove the necessity for traditional "hook and loop" fastener systems, thereby improving the ability to clean the devices and decreasing the tendency for the fastening system to entrap microscopic and macroscopic debris and/or organisms.

In another aspect, apparatus and corresponding methods that employ discrete structures attached to a surface of one or more padding(s) and mating features, which are built into a limb support shell, are disclosed. The mating features can be mounting openings that are configured to accept these discrete structures and remain engaged to the discrete structures through a mechanical interference. The mating features can be manually engaged, holding the padding and the shell together as a combined system until manually disengaged by the user. While in use as a padded support system, the mechanical interference can provide sufficient resistance to prevent the pad from inadvertently disengaging from the shell during use.

In some aspects, a support structure for holding a patient's limb is disclosed. The support structure can comprise a shell configured to at least partially receive and support the patient's limb. The shell can comprise at least one mounting opening. The support structure can also comprise a padding coupled to the shell and configured to provide a protective surface for the patient's limb. The padding can comprise at least one mounting structure configured to be coupled to the mounting opening and coupling of the at least one mounting structure to the at least one mounting opening can be configured to provide an interference fit that secures the padding to the shell.

In another aspect, a method for providing a support structure for holding a patient's limb is disclosed. The method can include coupling at least one mating opening disposed on a surface of a shell configured for at least partially receiving the patient's limb with at least one mating structure of a protective padding via an interference fit and receiving the patient's limb on the protective padding.

In other examples, the aspects above, or any system, method, apparatus described herein can include one or more of the following features.

The shell can comprise at least one of a thermoplastic material, polyethylene, polypropylene, Acrylonitrile Butadiene Styrene (ABS), structural foam, and formed sheet metal.

The at least one mounting structure can comprise a base configured to be coupled with/connect to an outer surface of the padding and a neck extending substantially orthogonally from the base. The neck can comprise at least one interference ring. Further, the neck can be hollow and an insert can be configured for positioning in the hollow neck. Furthermore, the mounting structure can comprise at least one of a liquid injection molded silicone, thermoplastic elastomer, thermoplastic urethane, a rubber-like material, and a soft plastic.

Additionally, or alternatively, the at least one mounting structure can be disposed within at a predetermined distance from an edge of the padding. The predetermined distance can be any suitable distance. For example, in some embodiments, the predetermined distance can be less than or including three inches and/or less than or including five inches.

Further, in some embodiments, the mounting openings can be disposed at a predetermined distance from an edge of the shell. The predetermined distance can be any suitable distance. For example, the predetermined distance can be less than about five inches 5" from the edge of the shell.

Further, the at least one mounting opening can be configured to extend through a thickness of the shell. Additionally, or alternatively, the mounting structure can be configured to extend through an entire length of the at least one mounting opening. Further, the at least a portion of the shell can comprise an inner wall and an outer wall and the mounting opening can be disposed on the outer wall of the shell.

In some embodiments, the mounting structure can be configured to expand on an inner surface of the outer wall of the shell to secure the padding to the shell. Further, the at least one mounting structure can comprise at least one interference ring configured to provide the interference fit that secures the padding to the shell. Additionally, or alternatively, the at least one portion of the interference ring can be configured to be larger in diameter than a diameter of the at least one mounting opening in which the at least one mounting structure is received.

In some embodiments, the interference fit between an inner diameter of the mounting opening and an outer diameter of the mounting structure can be in a range varying from about 0.020 inches to 0.040 inches.

Additionally, or alternatively, the at least one portion of the mounting structure can comprise at least one of a generally square-shaped, a generally rounded, and generally triangular-shaped cross section. Further, in some embodiments, the at least one mounting structure comprises at least one extension configured to at least partially extend over an edge of the shell to couple the padding to an outer surface of the shell.

In some embodiments, the at least one extension can comprise a notch configured to engage a corresponding recess in the outer surface of the shell. Further, the notch and the corresponding recess can be compatibly shaped so as to mate with one another.

Other aspects and advantages of the invention can become apparent from the following drawings and description, all of which illustrate the various aspects of the invention, by way of example only.

DETAILED DESCRIPTION

Patient limb support devices are often configured to hold and/or support relevant portion(s) of a patient's body using a substantially rigid frame that has been padded to protect the patient's body/limb from the rigid frame. Such supporting devices are commonly used during surgical procedures (or during recovery or treatment), in which the patient's limb needs to be elevated or safely held in place. The padding covering the rigid surface is often held in place through attachment to the rigid support frame.

Figure 1:
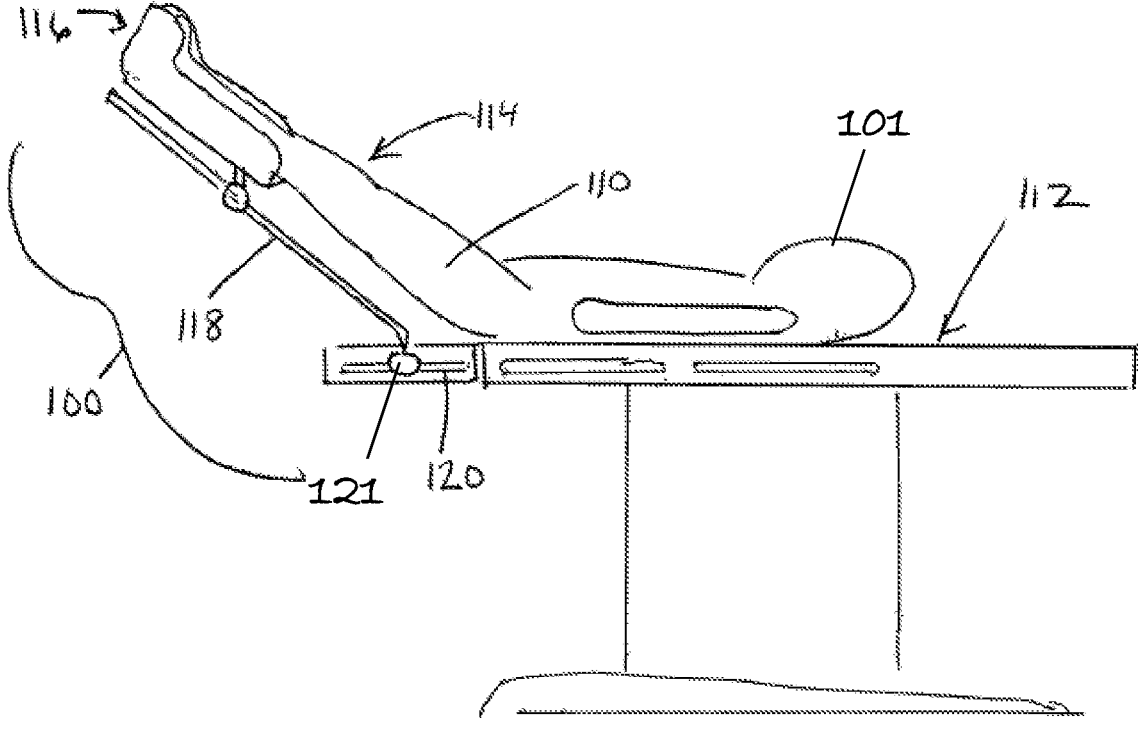
FIG. 1 schematically illustrates a limb holder according to some aspects disclosed herein.

FIG. 1 schematically illustrates a patient 101 in a lithotomy position. The term "lithotomy position," as used herein is intended to refer to a position (e.g., for surgical procedures or medical examinations), in which at least a portion of the patient's body 101 is maintained above or at the same level as the patient's hip. However, although described in terms of the lithotomy position and shown as supporting the patient's lower body, the embodiments disclosed herein can be used in conjunction with any support device, apparatus, system, or mechanism used to support, maintain in place, and/or hold any part or portion of the anatomical structure of a patient. The term patient, as disclosed herein, can refer to a human or an animal patient. Further, although described as being used during surgical procedures, the embodiments disclosed herein can be used to support a part of a patient's body at any point or time during examination, treatment, surgical procedures, and/or recovery.

Referring back to FIG. 1, a limb holder 100 according to some aspects herein is illustrated. The limb holder 100 can be used to support any portion of the patient's 101 anatomy (e.g., the patient's leg 110). For example, the limb holder 110 can be a lithotomy stirrup used to hold or elevate the patient's 101 leg 110. Although not shown in FIG. 1, it should be noted that depending on the application at hand, one or more limb holders 100 can be used (e.g., in a gynecological exam, a pair of limb holders 100 can be used). The limb holder 100 can be used to hold the patient's limb in space, relative to at least one surface 112 on which the remaining portions of the body of the patient 101 are disposed. Although the term bed 112 is used hereinafter to refer to the at least one surface, the surface 112 can be the surface of a bed, an operating table, an examination table, etc.

The limb holder 100 can comprise one or more support elements 116 that are used to support at least one part of the limb. For example, as shown in FIG. 1, the limb holder 100 can comprise a support element 116 (formed to resemble the rear portion of a boot in the example shown in FIG. 1) configured to support the lower portion 114 of the patient's leg 110. In some implementation, the support element 116 can be configured to support the at least one portion 114 of the limb by wrapping around and/or cradling the portion 114 of the limb. The support element 116 can be padded to prevent injury to the patient.

The limb holder 100 can further comprise a support structure 118 that is configured to be coupled to the bed 112 via a mounting rail 120. Generally, any suitable means available in the art can be used to connect and mount the support structure 118 to the mounting rail 120. For example, one or more clamps 121 can be used to connect the support structure 118 to the mounting rail 120. Generally, any suitable clamp or connecting mechanism can be used. However, the type of clamp or connecting mechanism used can depend on the required mating geometry (e.g., the type or shape of the corresponding mating/mounting features on the mounting rail 120 and/or the support structure 118) and/or the desired range of motion (the range of motion of the device 100).

Figure 2:
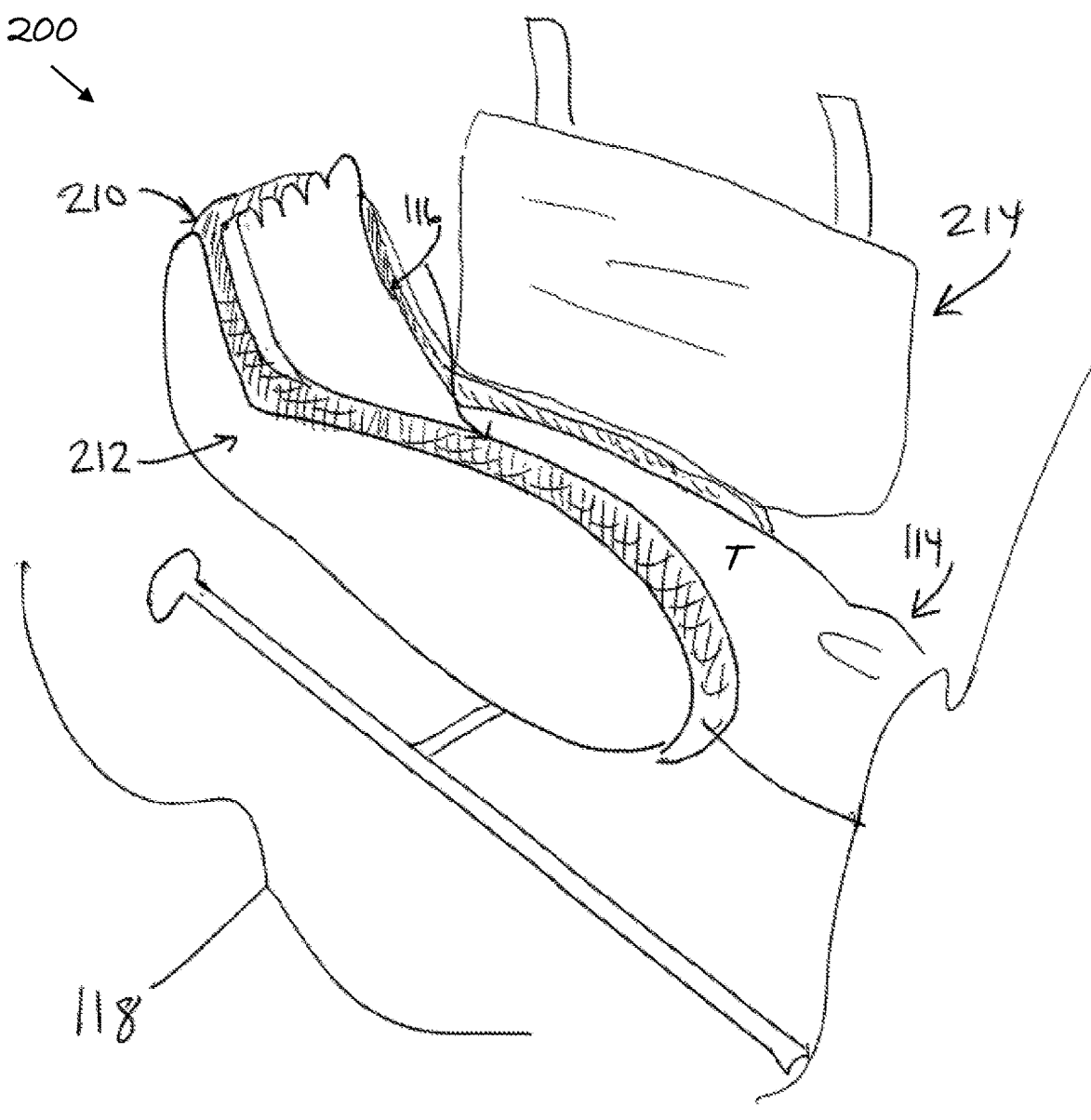
FIG. 2 schematically illustrates a limb holder according to some embodiments disclosed herein.

FIG. 2 illustrates a limb holder 200 according to some embodiments disclosed herein. As noted previously, although shown as supporting a leg of the patient, the limb holder 200 can be used to support any limb and/or body part of the patient. Further, the limb holder 200 can comprise any shape or size. For example, as shown in FIG. 2, the limb holder 200 can comprise a semi boot-shaped support element 116 that is configured to support a portion 114 of the patient's limb (e.g., leg). The support element 116 can be padded and configured to cradle the patient's limb.

Specifically, the support element 116 can comprise a shell 212. The shell 212 can be coupled to the support structure 118 via any suitable means available in the art. The shell 212 can also be configured to support one or more padding(s) 210. The padding 210 can comprise any suitable padding or cushioning material. The padding 210 can be configured such that it is removable and/or replaceable. Specifically, as described with respect to FIG. 3, the padding 210 can be configured such that it can be separated from the shell 212.

The support element 116 can further comprise a cover 214. The cover 214 can be removably and replaceably or permanently coupled to the support element 116. Alternatively, or additionally, the cover 214 can be configured to be movable with respect to the support element 116. Generally, any suitable available mechanism can be used to couple the cover 214 to the support element 116 and/or provide the cover with the required movement with respect to the support element 116.

The cover 214 can be configured such that it covers at least one portion of the patient's limb that is not covered and/or cradled by the support element 116. For example, as shown in FIG. 2, the support element can comprise a half-boot structure that leaves the top portion T of the patient's limb exposed/uncovered. The cover 214 can be configured, as shown in FIG. 2, to cover at least one part of the portion T that is not covered by the support element 116. The cover 214 can function to protect the patient's limb (body) from possible and/or inadvertent, unwanted impact that may occur during care, operation, treatment and/or recovery.

As noted, the cover 214 can be an integral part of the support element 116 and permanently coupled to the support element 116. Alternatively, the cover 214 can be a removable, replaceable, and independent component that is coupled via suitable mechanical means to the support element 116. Further, although shown as being coupled to the side of the support element, the cover 214 can be coupled to any suitable part of the support element 116.

The shell 212 can comprise any suitable available material. For example, the shell 212 can comprise at least one of a thermoplastic material (e.g., polyethylene, polypropylene, or Acrylonitrile Butadiene Styrene (ABS)), structural foam, or formed sheet metal. Generally, the shell 212 can be manufactured via any suitable manufacturing process such as injection molding, rotational molding, thermoforming, or vacuum forming.

Figure 3:
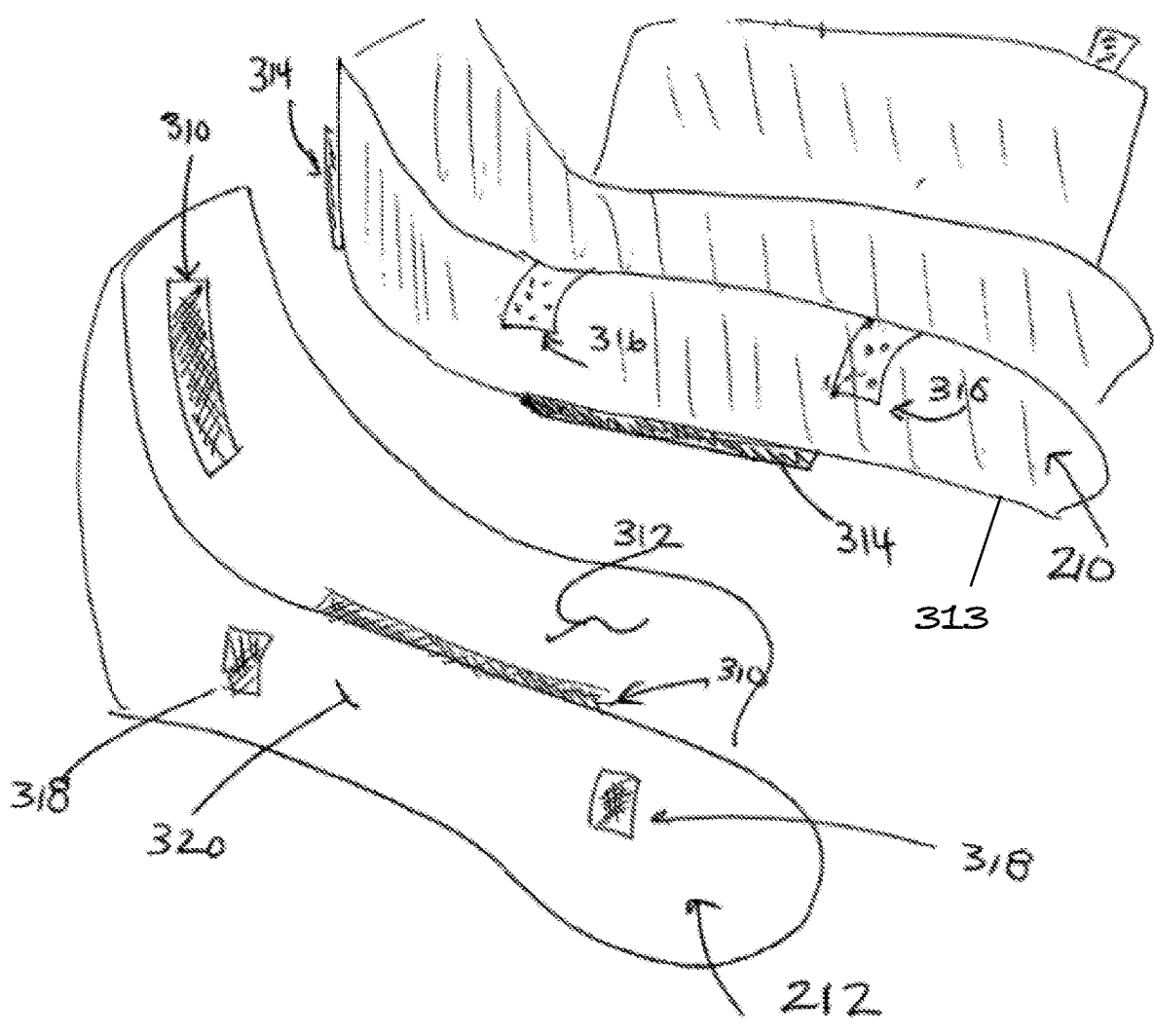
FIG. 3 schematically illustrates an exploded view of a support element.

FIG. 3 schematically illustrates how a shell 212 of a support element 116, such as the support element shown in FIG. 2, can secure a padding 210. In the example shown in FIG. 3, the shell 212 is shown separately from the padding 210. Generally, any suitable means available in the art can be used to connect and secure the padding 210 to the shell 212. For example, traditionally, one or more fasteners (e.g., Velcro® brand fasteners or hook and loop fasteners) are used to secure the padding 210 to the shell 212.

In the example shown in FIG. 3, a hook 310 is attached to an inside surface 312 of the shell 212. Generally, any suitable means can be used to connect the hook 310 to the shell. For example, an adhesive, one or more staples, one or more screws, or a combination thereof can be used to secure the hook 310 to the surface 312. Similarly, a loop 314 can be attached to underside surface 313 of the padding 210 in an area corresponding to the area of the shell 212, to which the hook 310 is attached. The loop 314 can be attached to the padding using any suitable means available in the art. For example, the loop 314 can be sewn and/or adhered to the padding 210. Further, the lateral and medial sides of the padding 210 can be secured using loop flaps 316 to corresponding hook patches 318 on an outer surface 320 of the shell 212.

Figure 4A:
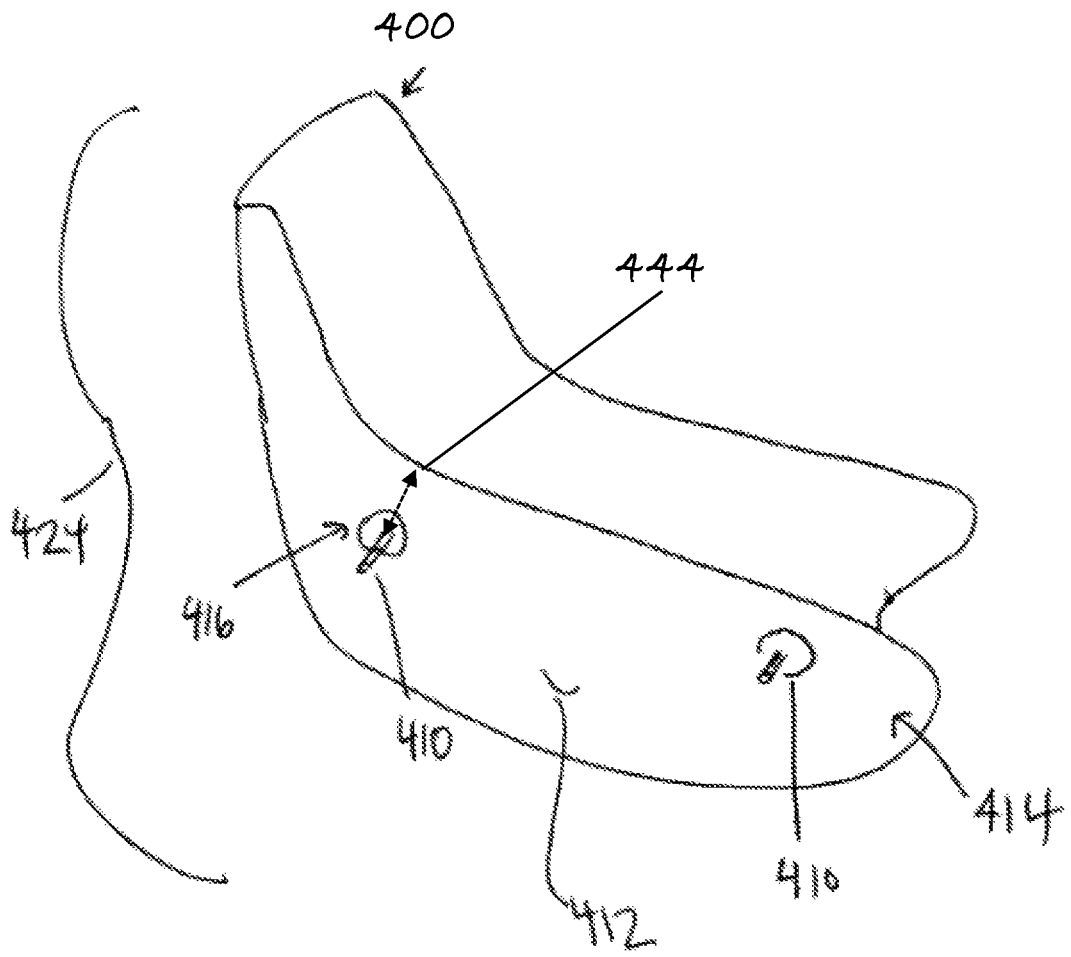
FIG. 4A schematically illustrates a front view of a support element padding according to some embodiments disclosed herein.
Figure 4B:
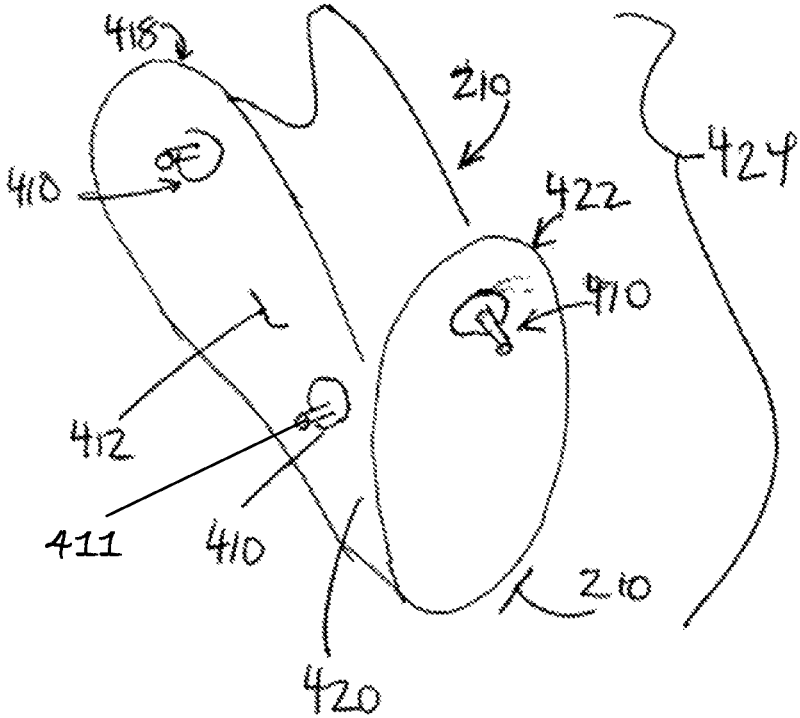
FIG. 4B schematically illustrates a rear view of a support element padding according to some embodiments disclosed herein.

FIG. 4A-4B illustrate a padding 400 according to some embodiments disclosed herein. Although described as having a single padding 400, one or more paddings 400 can be used with embodiments disclosed herein. As shown in FIG. 4A, which illustrates a front view of the padding 400, the padding 400 can comprise one or more mounting structures 410 secured to an outer surface 412 of the padding 400. Generally, any suitable number of mounting structures 410 can be used and the mounting structures 410 can disposed at any suitable location on the outer surface 412 of the padding 400. For example, as shown in FIG. 4A, at least mounting structure 410 can be disposed within a predetermined distance d1 from at least one portion of an edge 444 of the padding 400. For example, in some implementations, the distance d1 is configured such that it is less than or including three inches (d1≤3") and/or less than or including five inches (d1≤5"). Limiting the distance d1 to ≤5 can provide certain advantages. For example, limiting the distance can reduce possible dislodgment of the padding 400 from the shell 500 (shown in FIG. 5) due to axial forces exerted on the padding 400 as the patient's limb is secured by the limb holder.

The mounting structures 410 can be in the form of protruding pins that can be inserted into respective mounting openings 510 (shown later in FIG. 5) to secure the padding 400 to a shell 500 (later shown in FIG. 5). For example, in the embodiment shown in FIG. 4A, the mounting structures 410 are disposed on the outside of the lateral wing 414 and near the lateral ankle section 416 of the padding 400. Additional mounting structures 410 can also be utilized. For example, as shown in FIG. 4B, the padding 400 can include any number of mounting structures 410 (for example, three structures as shown in FIG. 4B) on an outside surface of the medial wing 418, on a medial ankle section 420, and on an outer surface of the upper toe section 422. Generally, any number of mounting structures 410 can be used. The number of mounting structures 410 can depend on the level of mounting security that the padding 400 is desired to have, once mounted and secured by the shell 500 (shown in FIG. 5).

The mounting structures 410 can be secured to the surface of the padding 400 using any suitable means available in the art, such as but not limited to adhesives, sewing, and/or other physical and/or chemical means. Alternatively or additionally, the mounting structures 410 can be molded into the padding 400, passed through hole(s) disposed in the padding (not shown), or upholstered in the padding 400.

The mounting structures 410 can be configured such that they are only exposed on the outer surface 412 of the padding 400. The exposed surfaces 411 of the mounting structures 410 are, therefore, the only surfaces that need to be cleaned, disinfected, and/or kept sterile. Further, since the external surfaces 411 of the mounting structures 410 are configured such that they protrude/project out of the padding, these surfaces can be easily cleaned using common methods for disinfecting surfaces in hospitals and/or operating rooms. Accordingly, by utilizing mounting structures 410 as disclosed herein, embodiments of the present disclosure reduce and minimize potential entrapment of debris or organisms in the padding, thereby providing superior means for securing the padding 400 to the shell 500 over commonly used hook and loop fastening systems with regard to infection control.

The mounting structures 410 can be configured for mating with corresponding mounting openings of a shell. FIG. 5 schematically illustrates a shell 500 according to some embodiments disclosed herein. As shown in FIG. 5, the shell 500 can comprise a plurality of mounting openings 510 each configured to receive a corresponding mounting structure 410 of the padding 400. As explained with reference to the mounting structures 410, generally any number of mounting openings 510 can be used and the mounting openings 510 can be disposed at any suitable location on the shell 500. Further, the number of mounting openings 510 and the mounting structures 410 need not be the same. For example, in some embodiments, the shell 500 can have more mounting openings 510 than the mounting structures 410 provided in the padding 400. Generally, the number of mounting openings 510 utilized can depend on the level of mounting security that the padding 400 is desired to have, once mounted and secured by the shell 500. By way of example, the number of mounting structures 410 and the mounting openings 510 can be in a range of about two to about ten, although other numbers of mounting structures 410 and mounting openings 510 can be used.

The mounting openings 510 can comprise any suitable shape and size. The openings 510 can further be configured such that they can accommodate the size and shape of the mounting structures 410. Generally, the location of the mounting openings 510 on the shell 500 can be configured to ensure that they correspond to and/or match the locations of the mounting structures 410 on the padding 400.

Further, the mounting openings 510 can be configured to be through holes. Specifically, the mounting openings 510 can be configured such that they pass through from the inner surface 512 to the outer surface 514 of the boot shell 500. The mounting openings 510 can further be configured to provide a mechanical interference fit with the mounting structures 410 on the padding 400.

Figure 5:
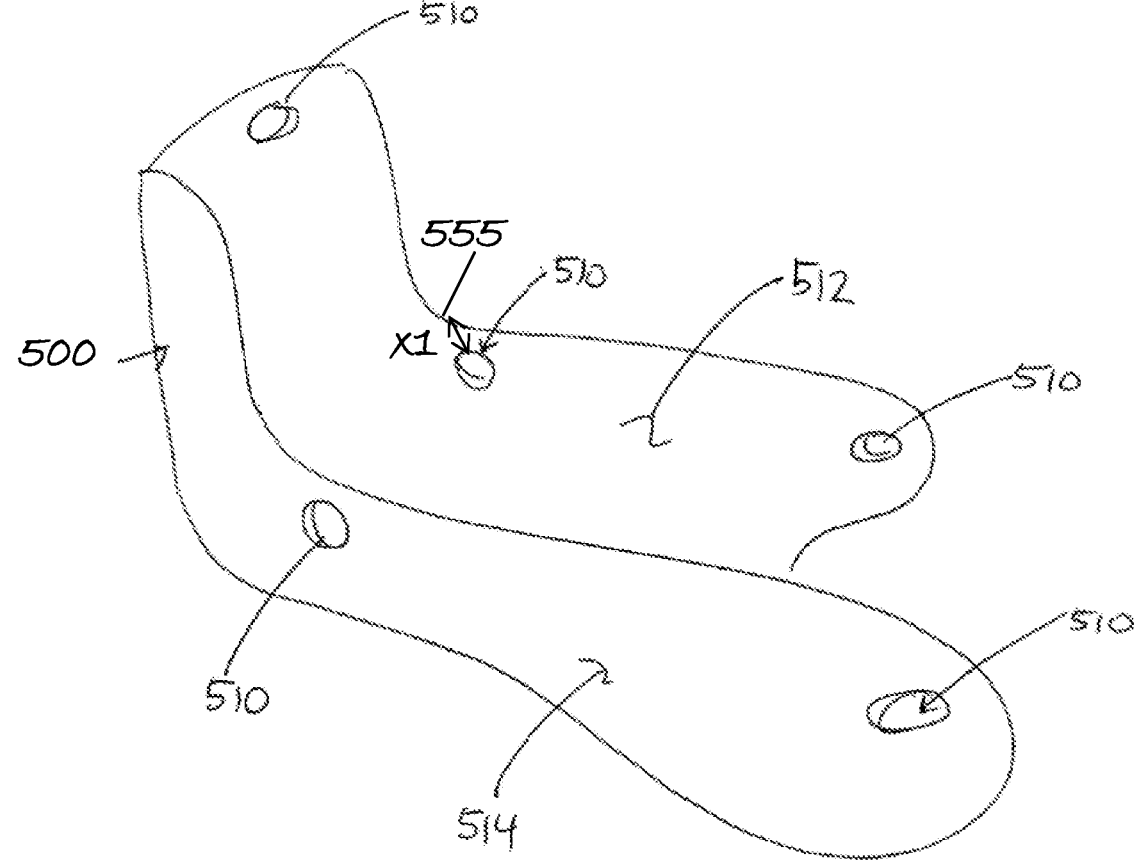
FIG. 5 schematically illustrates a shell according to some embodiments disclosed herein.

For example, as shown in FIG. 5, at least mounting opening 510 can be disposed within a predetermined distance x1 from at least one portion of an edge 555 of the padding 500. The distance x1 can be any suitable distance. For example, in some implementations, the distance x1 is configured such that it is less than or including three inches (x1≤3") and/or less than or including five inches (x1≤5").

Figure 6:
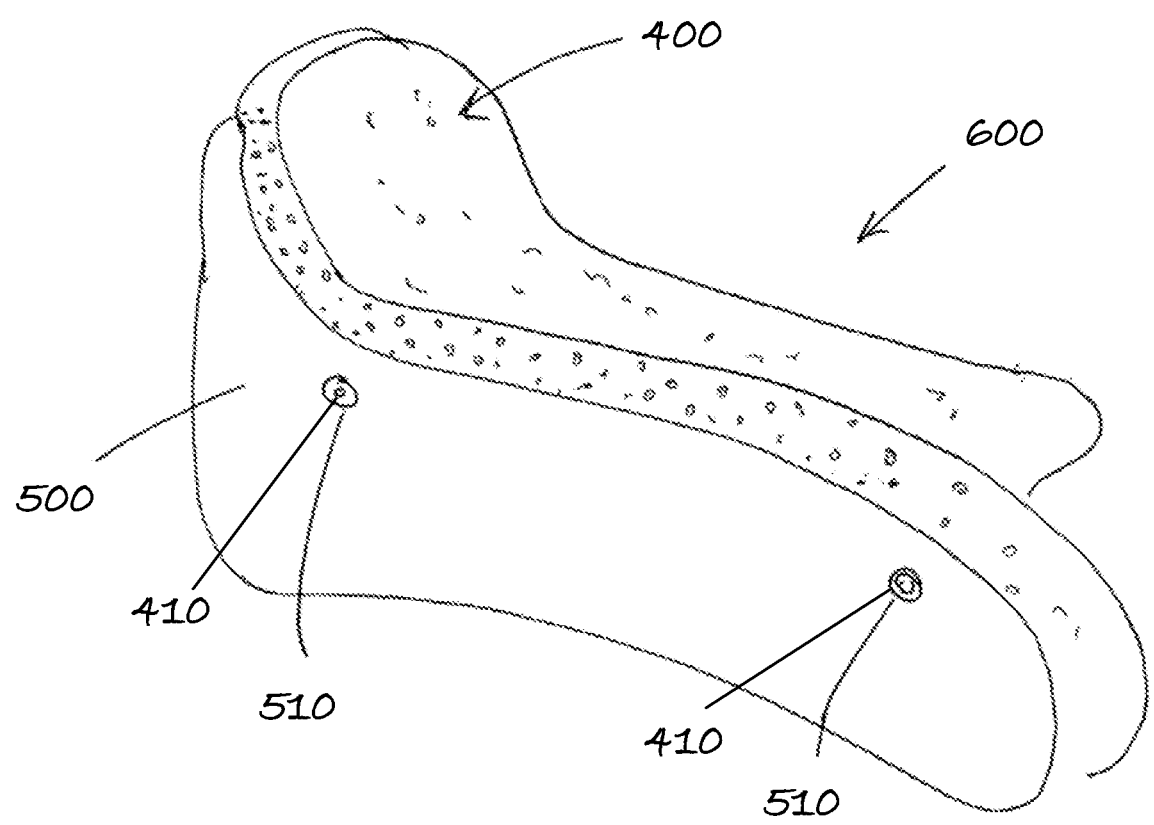
FIG. 6 schematically illustrates a limb holder according to some embodiments disclosed herein.

FIG. 6 schematically illustrates a limb support 600 according to some embodiments disclosed herein. As shown, the limb support 600 comprises a padding 400 that is secured to an inner surface of a shell 500 via an interface fit between the mounting structures 410 of the padding 400 and mounting openings 510 of the shell 500. The interface fit is formed via engagement between a given mounting structure 410 and a corresponding mounting opening 510.

Figure 7A:
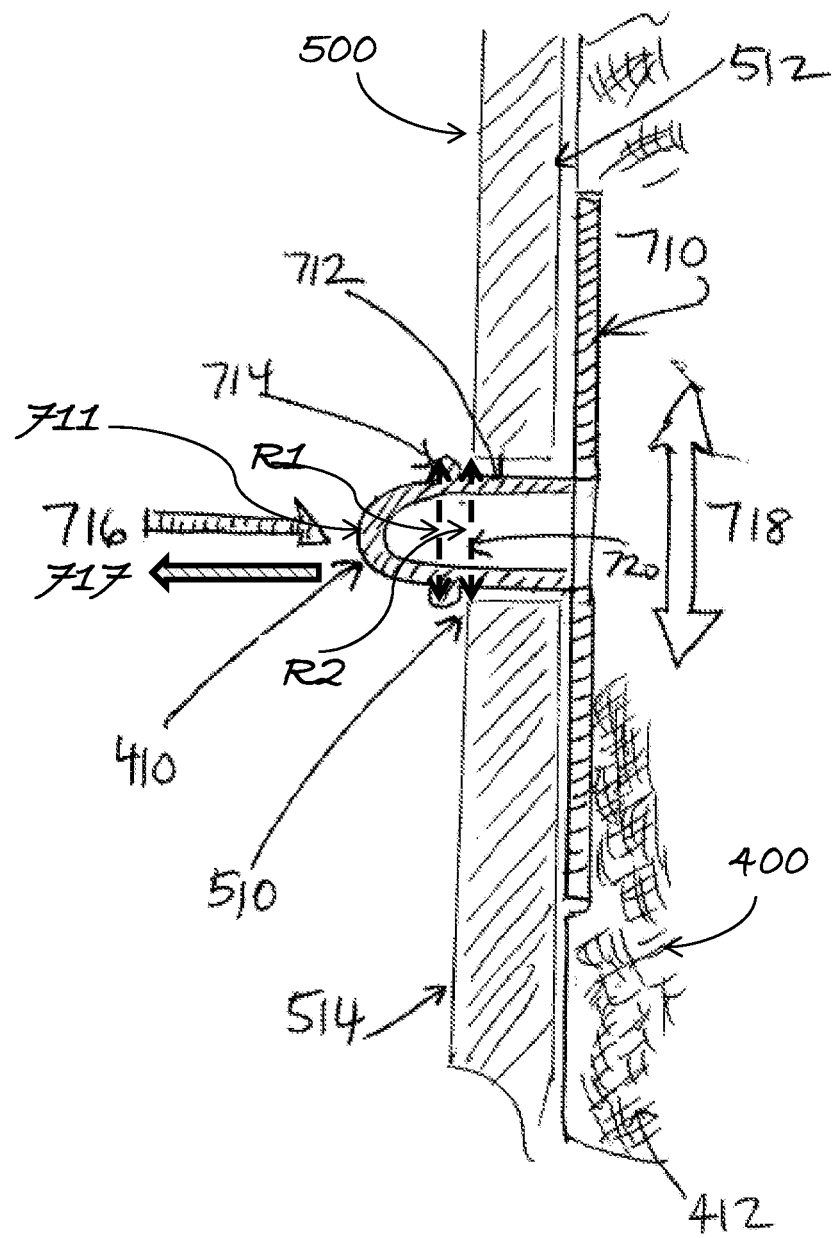
FIG. 7A schematically illustrates a cross-section of a mounting structure secured in a mounting opening via an interface fit according to embodiments disclosed herein.

FIG. 7A schematically illustrates a cross-sectional view of interface fit established via engagement of a mounting structure 410 and a mounting opening 510. As shown, a mounting structure 410 can comprise a base 710 disposed and attached to an outer surface 412 of the padding 400. The mounting structure 410 can further comprise a neck section 712 configured to protrude substantially perpendicularly out of the base 710 of the mounting structure 410.

Figure 7B:
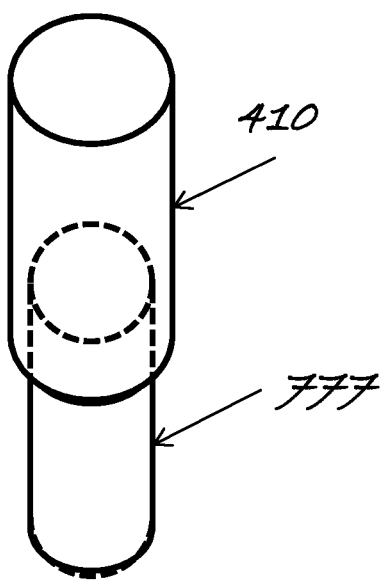
FIG. 7B-7G schematically illustrate several examples of mounting structures according to some embodiments disclosed herein.

In some embodiments, the neck section 712 can be hollow and configured to receive an insert. Specifically, as shown in FIG. 7B, the neck section 712 can be hollow and configured to receive an insert 777 to allow the mounting structure 410 to flex to accommodate any variation between the location of the attachment of the mounting structure 410, on the outer surface 412 of the padding 400, and the location of the mounting opening 510 on boot shell 500. More particularly, the mounting structure 410 can be a hollow and/or flexible structure that can be flexed and/or slightly moved and inserted into a corresponding mounting opening 510. This allows for the mounting structure 410 to be capable of passing through a corresponding mounting opening 510 even if the mounting structure 410 and the mounting opening 510 are not perfectly aligned. Once inserted into the mounting opening 510, an insert 777 can be inserted into the hollow mounting structure 410 to reinforce the structure and secure the padding against the shell. The insert can comprise any suitable material known in the art. Further, in some embodiments, the insert can be disposable. In some embodiments, the insert 777 can be more rigid than the hollow mounting structure 410. Further, the insert 777 can comprise any suitable material, for example, a polymeric material.

Alternatively, the neck section 712 can be solid and configured to allow the mounting structure 410 to be easily passed through mounting opening 510.

The mounting structure can further comprise an interface ring 714 that is slightly larger in diameter R1 than the diameter R2 of the mounting opening 510 that is receiving the mounting structure 410. In some implementations, the interface ring 714 can be configured to have a diameter R1 that is slightly larger than the diameter R2 of the mounting opening 510. For example, in some embodiments, the diameter R1 can be about 0.02 inches to about 0.04 inches larger than the diameter R2. In other implementations, the diameter R1 can be about 0.02 inches to about 0.09 inches larger than the diameter R2.

The interface ring 714 can be disposed at any suitable location on the mounting structure 410 and configured such that it is exposed on the surface of the shell 500 and engages the outer surface 514 of the shell 500. In some implementations, the interface ring 714 can be exposed near a tip 711 of the mounting structure 410, for example in a location disposed at a distance about between 0.11 inches to 0.33 inches from the tip 711. In some implementations, the mounting structure 410 can be configured such that it protrudes between 0.5 inches to 3.5 inches from the outer surface 412 of the padding 400 in order to secure the padding 412 to the shell 500.

As noted, the mounting openings 510 of the shell 500 can comprise any suitable shape. For example, the mounting openings 510 can be circular, elliptical, triangular, and/or trapezoidal. Further, the mounting openings 510 can be implemented in the shell using any suitable technique available in the art. For example, the mounting openings 510 can be bored, cut, or molded into the shell 500. The circumference 720 of at least one mount opening 510 can be configured to allow the interference ring 714 to compress inward while passing through the mounting opening 510. The interference ring 714 can be configured such that, once passed through the mounting opening 510 and the circumference 720 of the mount opening 510, the interference ring 714 expands outwardly to secure the padding 400 against the outer surface 514 of the shell 500.

The engagement of the interference ring 714 and the mounting opening 510 forms a mechanical interference fit configured to resist an incidental axial force 716 caused, for example, as a result of inserting a patient's limb into the shell 500. The incidental axial force 716 can, alternatively or additionally, be caused from inadvertent pressure resulting from users leaning or pushing against the mounting structure 410 or force exerted by other equipment used in conjunction with the limb holder and/or pushing against the mounting structure 410.

The mechanical interference fit between the neck section 712 and the inner surface of the mounting opening 510 thereby provides a resistive counter force 717 configured to restrict relative lateral movement 718 of the outer surface 412 of the padding 400 and the inner surface 512 of the shell 400, such as lateral force caused by movement of the patient's limb(s) against the padding 400, or adjustment of the padding 400.

Generally, the mounting structure 410 can comprise any suitable material. For example, the mounting structure 410 can comprise a molded flexible material including but not limited to liquid injection molded silicone, thermoplastic elastomer, thermoplastic urethane, or other rubber-like materials. Flexible, rubber-like materials can allow for repeated compression and expansion of the mounting structure 410 without permanent deformation, allowing the engagement to be established and released repeatedly.

Generally, the interference fit between the inner diameter R2 of the mounting opening 510 and the outer diameter R1 of the mounting structure 410 can be any suitable size. The size of the interference fit can depend on the material selected to construct the mounting structure 410 and the desired strength of the intimate engagement while resisting axial forces 716. For example, in some implementations, the interference fit can be between 0.020" and 0.040" or between 0.010" and 0.080".

Figure 7C:
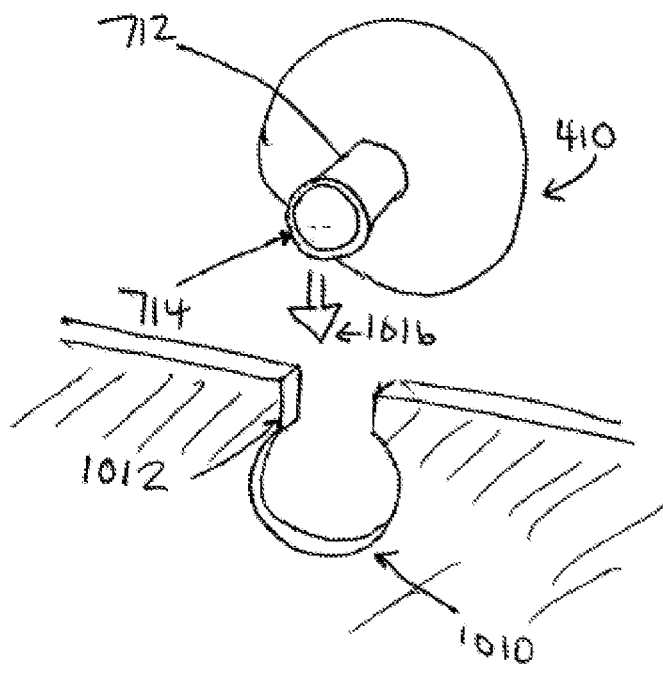
Figure 7D:
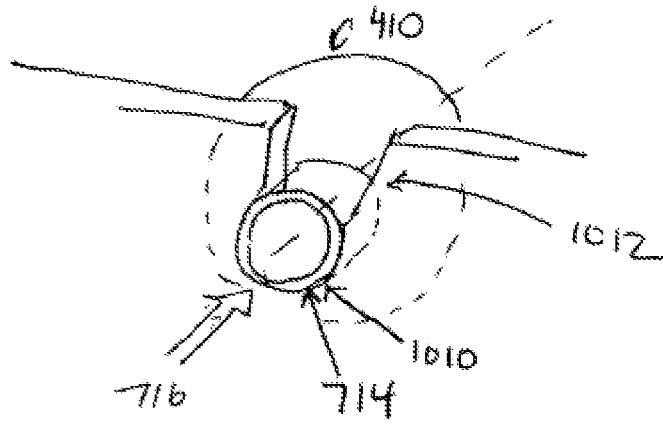
Figure 7E:
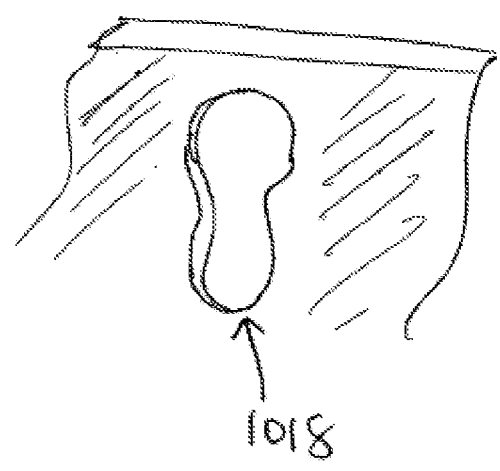

As noted above, mounting structures and mounting openings disclosed herein can comprise any suitable shape and size and be disposed at any suitable location on the shell and/or the padding. For example, as shown in FIG. 7C, the mounting opening can be a slot 1012 having a seat 1010 configured to receive the neck portion 712 of a mounting structure 410. The padding 400 can be secured against the shell 500 by pressing/pushing the neck 712 of the mounting structure 410 in a downward motion 1016 through the slot 1012, overcoming an interference fit between the outer dimensions of the neck 712 and the inner dimension of the slot 1012 until the neck 712 is seated in the seat 1010. As shown in FIG. 7D, once the mounting structure 410 is positioned within the seat 1010, the dimensional interference retains the neck 712 from moving opposite the direction of the arrow 1016, while the dimensional interference between interference ring 714 and the seat 1010 resists the incidental axial force 716 thereby securing the mounting structure 410 in the slot 1012.

Figure 7F:
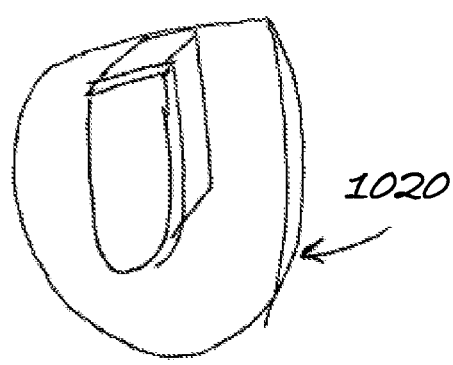
Figure 7G:
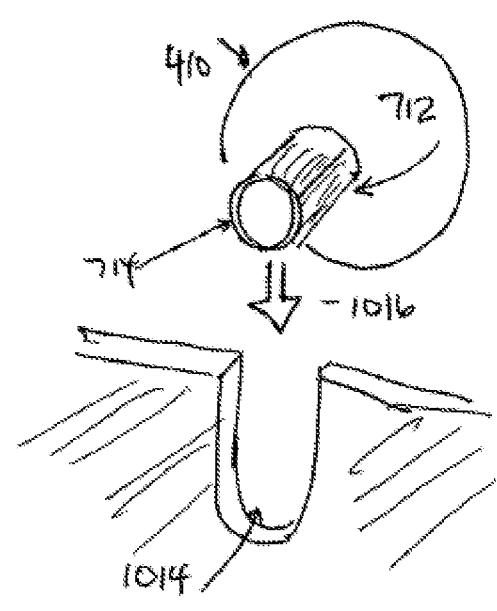

Further, as shown in FIGS. 7D-7G, the mounting opening can comprise any suitable shape, including but not limited to a key-hole shaped slot 1018 (shown in FIG. 7E) and/or a U-shaped slot 1014 (shown in FIG. 7G).

Generally, mounting structures 410 can comprise any suitable shape required to accommodate the shape of their corresponding mounting openings. For example, as shown in FIG. 7F, in implementations that utilize a key-hole shaped slot 1018 (FIG. 7E), a mounting structure 1020 having an accommodating shape (e.g., a key-shaped configuration) can be used, which can allow the mounting structure to mate with the respective opening so as to couple the padding to the shell. The key-shaped mounting structure 1020 can be configured such that it can be pushed through the key hole slot 1018. Further, the key-shaped mounting structure 1020 can be configured to be oversized relative to the key-hole shaped slot 1018. Specifically, the key-shaped mounting structure 1020 can comprise a flexible material, and be configured to have a similar shape as the key-hole shaped slot 1018 but be slightly oversized relative to the key-hole shaped slot 1018. The difference in the size between the key-shaped mounting structure 1020 and the key-hole shaped slot 1018 allows the flexible key-shaped mounting structure 1020 to expand once in the key-hole shaped slot 1018, thereby securing the padding, on which the key-hole shaped slot 1018 is disposed, to the shell, on which the key-hole shaped slot 1018 is disposed.

Similarly, as shown in FIG. 7G, a U-shaped slot 1014 with a corresponding mounting structure 410 having an accommodating shape can be utilized. The U-shaped slot 1014 can be disposed at any suitable position on the shell 500. For example, as shown in FIG. 7G, the U-shaped slot 1014 can be positioned at an upper edge of the shell 500 such that mounting structure 410 with the neck 712 and interference ring 714, attached to padding 400, can be moved downward, along a direction 1016, to secure padding to boot shell 500 (not shown).

FIGS. 8A-8H schematically illustrate non-limiting examples of mounting structures 410 that can be used with the embodiments disclosed herein. As shown and noted previously, the mounting structure can comprise any suitable shape and size known and available in the art. The neck section 712 of the mounting structure 410 can also comprise any suitable shape and size known and available in the art. For example, the mounting structure 410 can comprise a neck cross-section having a square 810 (FIG. 8A), triangular 812 (FIG. 8B), and non-rectilinear 814 (FIG. 8C), or circular 816 (FIG. 8D) shape.

Figure 8A:
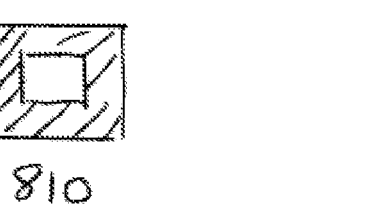
FIGS. 8A-8H schematically illustrate several examples of mounting structures according to some embodiments disclosed herein.
Figure 8B:
Figure 8C:
Figure 8D:
Figure 8E:
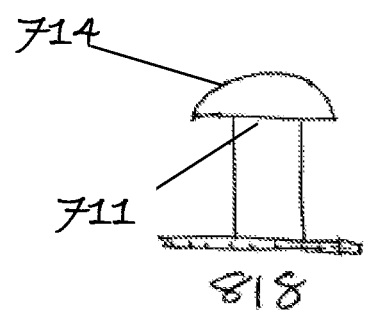
Figure 8F:
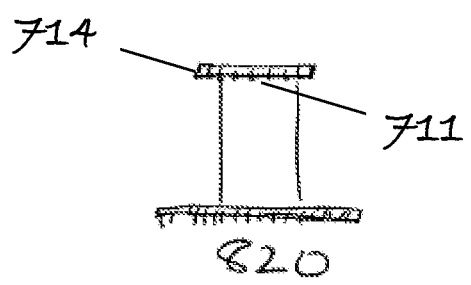
Figure 8G:
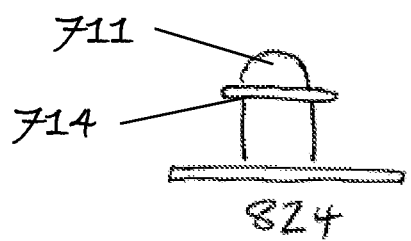
Figure 8H:
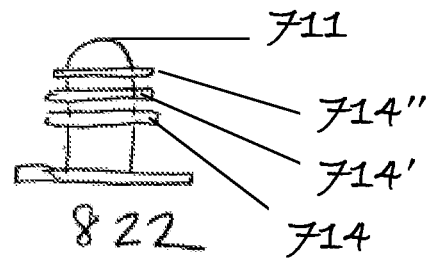

Further, the interface ring 714 can comprise any suitable shape and/or size known and available in the art and be disposed at any suitable position on the mounting structure 410. For example, as shown in FIGS. 8E-8F, the interface ring 714 can be positioned at or near the tip 711 of the mounting structure 410. Alternatively or additionally, as shown in FIG. 8G, the interference ring 714 can be positioned at any location below the tip 711 of the mounting structure 410. Further, as shown in FIG. 8H, the mounting structure 410 can comprise one or more interference rings 714, 714', 714". Furthermore, the interference ring 714 can comprise any suitable size and shape available in the art. For example, as shown in FIGS. 8E-8F, the interference ring 714 can comprise a rounded tip (FIG. 8E) or a flat tip (FIG. 8F).

Figure 9A:
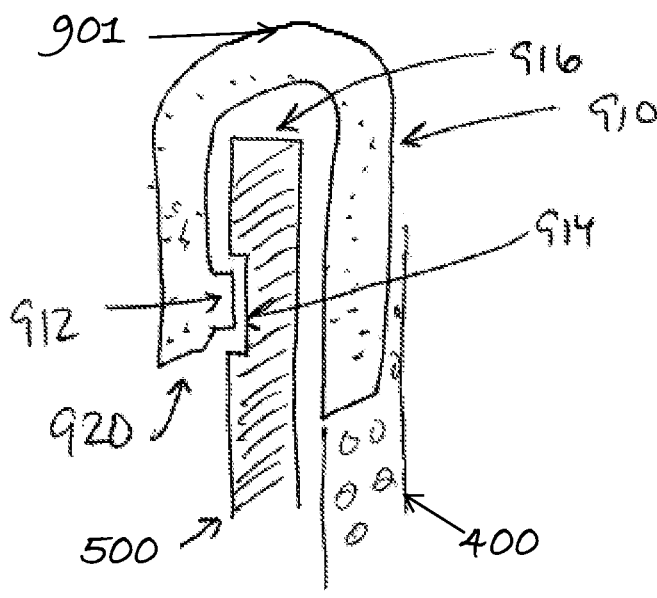
FIGS. 9A-9E schematically illustrate examples of mounting structures according to some embodiments disclosed herein.

Additionally, or alternatively, a bent-shaped mounting structure can be used to couple the padding 400 to the shell 500. For example, as shown in FIG. 9A, a mounting structure 910 can comprise a rounded (or bent) portion 901 that is configured to clip and extend over an edge 916 of the shell 500. The rounded portion of the mounting structure that clips and extends over the edge 916 of the shell 500 can comprise a protrusion or a nub 912 that is configured to mate with a corresponding indentation (notch) 914 disposed on the outer surface 514 of the shell 500. Regardless of whether the mounting structure comprises the nub 912 and/or whether the shell comprises the notch 914, the mounting structure 910 can be configured such that upon being passed over the edge 916 of the shell, the mounting structure 910 remains flush with the edge 916.

Figure 9B:
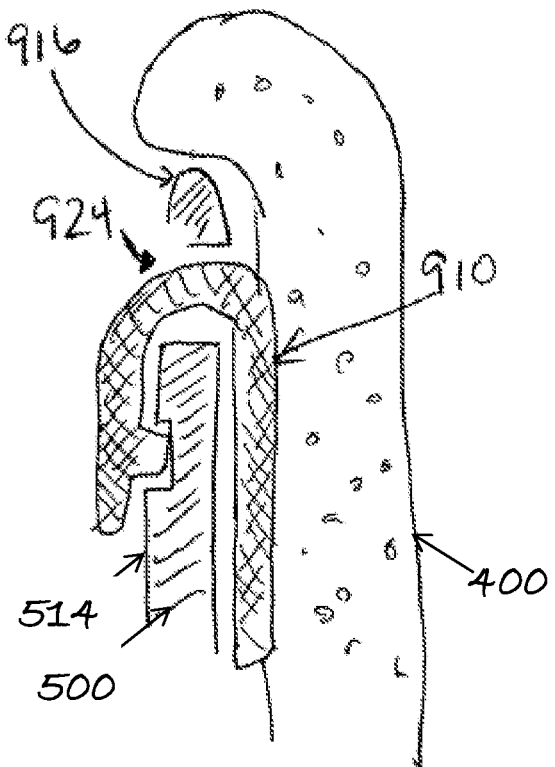

In some implementations, the shell 500 can include one or more through holes 924 configured to receive a bent-shaped mounting structure 910. Specifically, as shown in FIG. 9B, the shell 500 can include one or more through holes 924 configured to receive a portion of the mounting structure 910. The mounting structure 910 can be configured such that it can pass through the through hole 924 and clip over a portion of the outer surface 514 of the shell 500. The rounded portion of the mounting structure that clips and extends through the through hole 912 can comprise a nub 912 that is configured to mate with a corresponding indentation (notch) 914 disposed on the outer surface 514 of the shell 500.

In embodiments that utilize the nub and notch configuration, the mounting structure 910 can be coupled to the shell by engaging the nub 912 in the notch 914. Similarly, the mounting structure 910 can be disengaged from the shell by pulling an outer leg 920 of the bent mounting structure 910 to disengage the nub 912 from the compatibly shaped mating notch 914 and lift the bent mating structure off of the shell edge 916. Generally, the nub and notch can comprise any suitable shape and size and be disposed at any suitable location on the mating structure (nub) or the shell (notch).

Figure 9C:
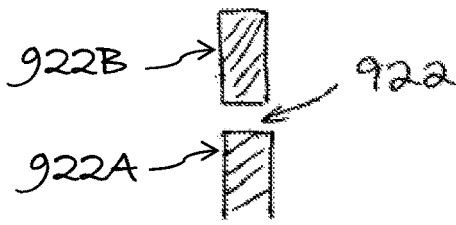

In some embodiments, the shell 500 can comprise a through hole 922. Specifically, as shown in FIG. 9C, the mounting indentation can be a through hole 922 that extends through a width of the shell 500. The through hole 922 divides the portion of the shell 500 upon which it is disposed to two portions 922A, 922B. The through hole 922 can be disposed at any suitable location on the shell 500, for example at a location near the edge 916 of the shell. In some implementations, the through hole 922 can be disposed at a position within five inches (5") of the upper edge of shell 500 in order to secure the upper edge of the padding 400 and prevent it from flopping inward.

Figure 9D:
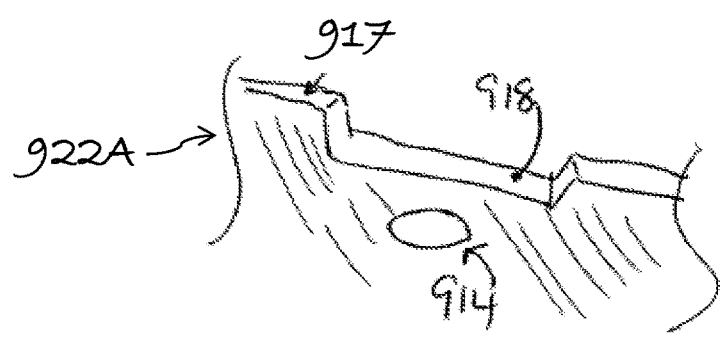
Figure 9E:
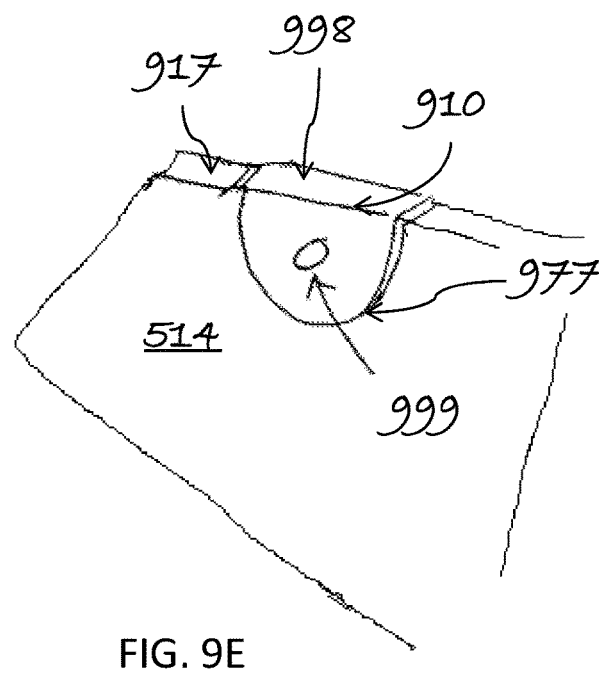

Further, as shown in FIG. 9D, the through hole 922 can comprise a notch 918 on at least one of its internal surfaces 917. Although shown as being disposed on one side 922A of the shell, the notch 918 can be disposed on the surface 917 of one or both 922A, 922B portions of the shell 500. The notch 918 can be configured such that it can receive a mounting structure 910 (shown in FIG. 9D). In this embodiment, the mounting structure 910 comprises an extension 977 that clips over the notch 918, disposed on the internal surface 917 of the shell portion 922A, and extends over the external/outer surface 514. Further, as shown in FIG. 9E, the extension 977 can comprise a mating feature 999 that is configured to mate with the indentation 914 disposed on the external surface 514 of the shell 500. The coupling of the mating feature 999 with the indentation 914 can further secure the padding to the shell. Specifically, a user can secure the padding 400 against the shell 500 by passing the extension 977 over the notch 918 (which can be a U-shaped notch) such that the extension extends over the surface/wall 514 of the shell. This configuration places the upper part 998 of the mounting structure 910 in the notch 918, thereby securing the mounting structure 910 against the surface 514 of the shell 500. The engagement of the mating feature 999 with the notch 914 can be utilized to further secure the padding to the shell. In some embodiments, the extension 977 can be configured such that upon passing of the extension 977 over the notch 918, the extension 977 is flush with the top edge of the shell.

The mounting structure 910 can be attached to the padding 400 using any suitable means available in the art. For example, the mounting structure 910 can be glued to the padding 400 and/or molded in the padding 400. Further, the mounting structure 998 can comprise any suitable configuration or materials and be formed using any suitable technique, including but not limited to injection molding (for thermos-plastics) or reaction injection molding (such as structural foam). In some implementations, the mounting structure 998 can be cut from any suitable material available in the art.

Figure 10A:
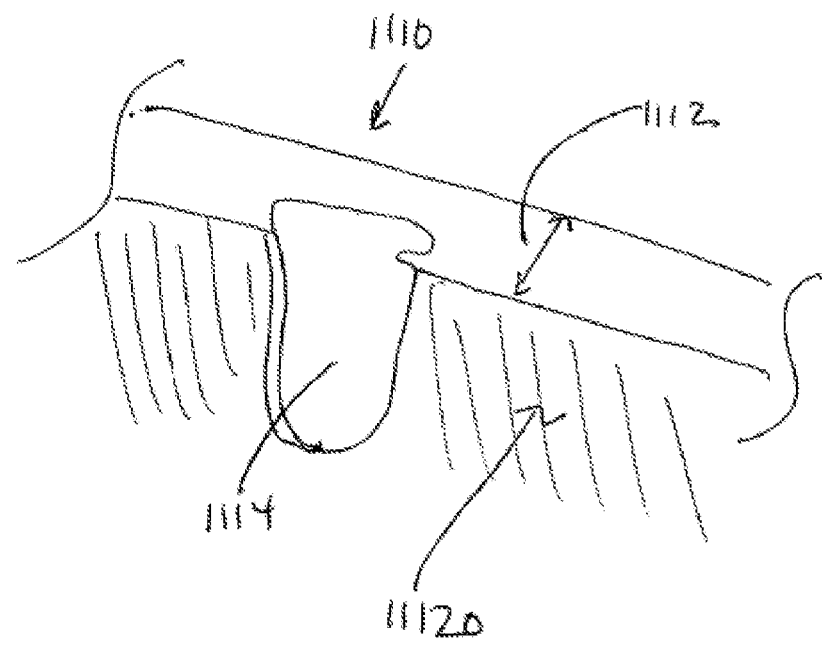
FIGS. 10A-10B schematically illustrate examples of a shell and a corresponding padding according to some embodiments disclosed herein.

FIG. 10A schematically illustrates a shell 1110 according to some embodiments disclosed herein. Generally, the shell can comprise any configuration or material and formed using any suitable manufacturing techniques, such as injection molding, roto-molding (for thermoplastics), or reaction injection molding (for structural foams). For example, the shell can be a double-walled or thick-walled structure 1110 having a thickness 1112 formed by an inner wall 1120, an outer wall 1116, and a space 1118 between the inner wall 1120 and the outer wall 1116. Alternatively, the shell can be a solid single layer or multi-layer structure.

The space 1118 can be a void space or a filled space. For example, the space 1118 can be filled with a foamed material. The space 1118 can be filled with material foamed based on the process used to form the shell, during or after manufacture of the shell. Some examples of such foamed material can include, without limitation, polyurethane, polyethylene, or Polyisocyanurate foams.

Figure 10B:
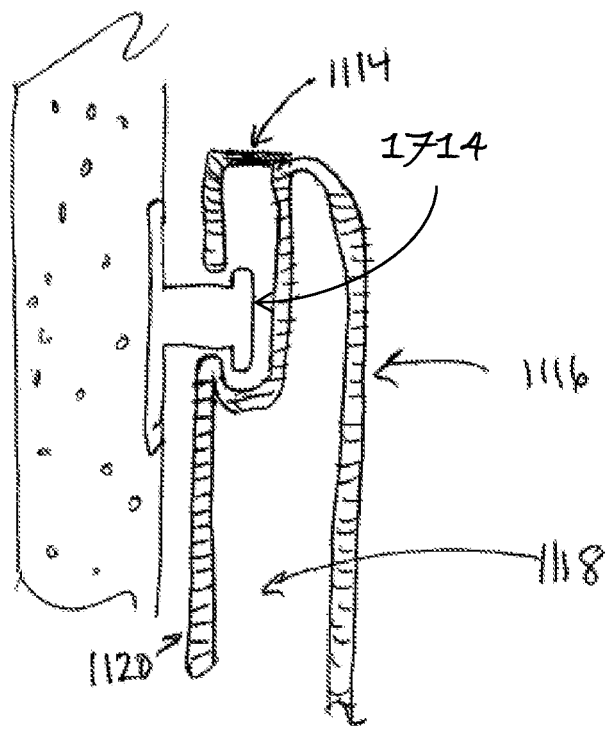

In some embodiments, the thickness of the shell can comprise a mounting feature 1114, which can be provided within the thickness of the shell and configured to receive and engage a mounting structure 410 of the padding. As shown in FIG. 10B, the mounting structure 410 can comprise an interference ring 1714 that is configured to expand, once passed through the opening of the mounting feature 1114, to secure the mounting structure 410 to the mounting feature 1114.

Although this specification discloses advantages in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment.

What is claimed is:

1. A surgical support structure for holding a patients' limb during a surgical procedure, the support structure comprising:

a shell configured to at least partially receive the patient's limb and support the patient's limb during the surgical procedure, the shell comprising at least one through hole; and a padding coupled to the shell and configured to provide a protective surface for the patient's limb, the padding comprising at least one mounting structure configured to pass through the at least one through hole;

wherein the shell further comprises an indentation disposed on an outer surface of the shell, the indentation being configured to receive a portion of the at least one mounting structure; wherein the portion of the at least one mounting structure extends through the at least one through hole; and wherein the portion comprises a nub configured to mate with the indentation.

2. The support structure of claim 1, wherein the shell comprises at least one of a thermoplastic material, polyethylene, polypropylene, Acrylonitrile Butadiene Styrene (ABS), structural foam, and formed sheet metal.

3. The support structure of claim 1, wherein the at least one mounting structure comprise at least one of a liquid injection molded silicone, thermoplastic elastomer, thermoplastic urethane, a rubber-like material, and a soft plastic.

4. The surgical support structure of claim 1, wherein the at least one through hole is disposed at a position within five inches of an upper edge of the shell.

5. The surgical support structure of claim 1, wherein the at least one through hole comprises a notch disposed on a least one internal surface of the at least one through hole.

6. The surgical support structure of claim 5, wherein the notch is configured to receive the portion of the at least one mounting structure.

* * * * *